United States Patent [19]

Boisde et al.

[11] Patent Number: 4,820,045
[45] Date of Patent: Apr. 11, 1989

[54] EQUIPMENT FOR THE EMISSION AND DISTRIBUTION OF LIGHT BY OPTICAL FIBERS, PARTICULARLY FOR IN-LINE SPECTROPHOTOMETRIC CONTROL WITH THE AID OF A DOUBLE BEAM SPECTROPHOTOMETER

[75] Inventors: Gilbert Boisde, Bures; Michel Quanquin, Montigny Le Bretonneux, both of France

[73] Assignee: Commissariat A L'Energie Atomique, Paris, France

[21] Appl. No.: 772,243

[22] Filed: Sep. 3, 1985

[30] Foreign Application Priority Data

Sep. 4, 1984 [FR] France .................................. 84 13611

[51] Int. Cl.[4] .............................................. G01J 3/42
[52] U.S. Cl. ................................................. 356/319
[58] Field of Search ........................ 356/319, 323–325, 356/402, 408–411, 414, 432–436, 447, 448; 250/227

[56] References Cited

U.S. PATENT DOCUMENTS

| | | | |
|---|---|---|---|
| 3,697,185 | 10/1972 | Kassel et al. | 356/410 |
| 4,509,212 | 4/1985 | Baker | 356/409 |
| 4,669,878 | 6/1987 | Meier | 356/319 |

FOREIGN PATENT DOCUMENTS

| | | |
|---|---|---|
| 0015170 | 9/1980 | European Pat. Off. . |
| 0062160 | 10/1982 | European Pat. Off. . |
| 0078882 | 5/1983 | European Pat. Off. . |
| 0109536 | 5/1984 | European Pat. Off. . |
| 2339166 | 8/1977 | France . |

OTHER PUBLICATIONS

Patents Abstracts of Japan, vol. 6, No. 70, (P—113), [948], 6 May 1982.
JP-A-57 302, (Sharp K.K.), 21-01-1982.
Patents Abstracts of Japan, vol. 4, No. 134, (P28), [616], 19 Sep. 1980.
JP-A-55 84 903, (Fujitsu K.K.), 26-06-1980.
Patents Abstracts of Japan, vol. 8, No. 55, (P-260), [1492], 13 Mar. 1984.
JP-A-58 204 343, (Tokyo Shibaura Denki K.K.), 29-1-1-1983.

*Primary Examiner*—F. L. Evans
*Attorney, Agent, or Firm*—Pearne, Gordon, McCoy & Granger

[57] ABSTRACT

Equipment for the emission and distribution of light by optical fibres, particularly for in-line spectrophotometric control with the aid of a double beam spectrophotometer, namely one channel for the reference and one channel for the measurement. It has at least one complementary light source emitting through a system of optical fibres permanently towards a reference cell and sequentially towards one of the n measuring cells corresponding to the controls to be performed, the light information from the reference cell on the one hand and sequentially from each of the n measuring cells on the other being passed by the system of optical fibres respectively to the reference channel and to the measuring channel of the spectrophotometer.

4 Claims, 6 Drawing Sheets

EQUIPMENT FOR THE EMISSION AND DISTRIBUTION OF LIGHT BY OPTICAL FIBERS, PARTICULARLY FOR IN-LINE SPECTROPHOTOMETRIC CONTROL WITH THE AID OF A DOUBLE BEAM SPECTROPHOTOMETER

BACKGROUND OF THE INVENTION

The present invention relates to equipment for the emission and distribution of light by optical fibres, particularly for in-line spectrophotometric control with the aid of a double beam spectrophotometer.

More specifically, the invention relates to an apparatus making it possible to e.g. determine the content of a certain number of substances within a solution by remote spectrophotometric analysis, the samples to be analysed not being located in the spectrophotometer sample compartment. This is for example the case when the solution to be analysed is radioactive and the cell containing the solution has to be placed within a protective enclosure, or in the remote control of industrial processes.

Among the methods for measuring chemical species in solutions or gases, spectrophotometric analysis is widely used in laboratories. In accordance with Beer's Law, it consists of measuring the light absorption linked, at a predetermined wavelength, with the concentration of the species to be dosed.

In the factory, in areas with a difficult access and more particularly in nuclear chemistry installations, this analysis method has become theoretically usable on an in-line basis, without transfer of samples to the laboratory, through optical fibres coming on to the market which make it possible to transfer information in the form of light from a measuring cell to a spectrophotometer, which can be at a varying distance from the measuring cell or cells, as a function of the circumstances.

The use of optical fibres connecting the measuring cell or probe, positioned in situ in a photometric analysis process consequently represents an advance leading to rendering commonplace equipment considered to be fragile in a corrosive industrial environment for reasons of chemical corrosion, deflagration or radioactivity.

To put this method based on optical fibres into effect, it is possible either to use photometers specially designed for remote measurement purposes, such as those marketed by the firm Hermann-Motriz under the registered trademarks Telephot and Crudmeter, or to equip commercially available spectrophotometers widely used in laboratories with an additional device, such as that described in European Pat. No. 0 015 170 granted on 6/22/83.

Such a known device is described diagrammatically with reference to FIG. 1, which shows a spectrophotometer with a sample compartment S having two beams, respectively designated R for the reference beam or channel and M for the measuring beam or channel. The admissions of light of intensity Io from the monochromator takes place at 2 and 3 in the insertion compartment 4 of the optical coupler. A system 5 of mirrors at 45° makes it possible to transmit this light both towards the optical reference probe 6 and through the fibre 7 to measuring cell 8. Probe 6 has a control sample making it possible to take account of the turbidity of the analysed solutions, i.e. all factors outside the material to be analysed which are liable to influence the absorption coefficient of the investigated solution. The light of intensity I'o leaving the optical reference probe 6 is reflected by mirrors 5 at exit 9 towards the not shown detector. The light of intensity I leaving the measuring cell 8 is reflected across the optical fibre 10 and mirrors 5 to the exit 11 and toward the same detector.

The measuring cell 8 is e.g. located in a protective enclosure 12 protecting it from the outside. This measuring cell 8 belongs to the control device of an industrial process, whose evolution is to be permanently monitored. The comparison of the intensities Io, I'o and I makes it possible to have information on the light absorption in measuring cell 8 due solely to the presence of the material to be analysed and consequently makes it possible to dose said material.

A known device like that shown in FIG. 1 suffers from a certain number of specific disadvantages, which will now be investigated. For this purpose, firstly certain general details will be given on the characteristics of optical fibres.

The transmission of an optical fibre varies with the wavelength and is a function of its composition (glass, plastic, silica with an index gradient or jump). The best transmission performances are presently obtained with synthetic silica fibres, the attenuation measured at $0.85\mu$ wavelength being approximately 1 decibel/km (dB/km).

By choosing optical fibres with predetermined characteristics, it is consequently possible to envisage carrying out photometric measurements at a distance of several hundred meters, but without eliminating the considerable light energy loss resulting from a device like that of FIG. 1.

Thus, apart from the transmission loss due to the actual fibre, there are certain light energy loss causes at the junctions of the fibres, (particularly in collimating lenses and also during reflections at the intake of the fibres).

Thus, on adding the losses due to the addition of fibres (10 dB) to the connectors and the partition passages (10 dB), and finally to the measuring cell (5 dB), the attenuation provided by a coupling device of a photometer by optical fibres can reach 25 dB. Converted into absorption units, this 25 dB loss represents an optical absorption of 2.5 absorptivity losses, whereas conventional commercial spectrophotometers permit measurements in the range 2 to 4 absorptivity units, i.e. with a beam intensity of $10^{-2}$ to $10^{-4}$ of that of incident light. This consequently leads to a limitation to uses, because it is necessary to deduct from the scale dynamics of the apparatus, the loss resulting from the coupling device. This disadvantage is particularly prejudicial in the case of a device like that of FIG. 1, whereof the only light energy source is the internal source of the spectrophotometer, initially designed for a measurement in the sample compartment S of the apparatus.

Another problem linked with in-line industrial control must also be mentioned. A device like that of FIG. 1 only makes it possible to monitor a single point in an installation with the aid of spectrophotometer 1. However, in industry there are numerous cases where the production process of a product requires a number of controls at several successive points during the production of this product and in this case, on transposing the apparatus of FIG. 1 to a construction of this type, it is necessary to have the same number of spectrophotometers as there are measuring cells. Although such an equipment would be theoretically possible, it would be very heavy and costly and it is obviously preferable, for economic reasons alone, to have only a single spectrophotometric analyser able to exploit the different measuring stations.

Finally, the last problem resulting from the in-line industrial control usage of these spectrophotometers, which are not designed for this purpose, is that of the life of the light source or sources incorporated into the apparatus. These sources which emit, either in the ultraviolet (deuterium source) or in the visible and near infrared (quartz-iodine source) have variable lives ranging from 50 to 2000 hours as a function of their characteristics.

Such a life is not a major disadvantage in the conventional use in a laboratory, because when necessary it is merely a question of replacing the faulty lamp. However, this is not so under continuous control conditions in a factory, where the interruption of the measurement is sometimes not possible for safety reasons.

SUMMARY OF THE INVENTION

The present invention specifically relates to equipment for the emission and distribution of light by optical fibres making it possible to overcome the aforementioned disadvantages and obtain by simple means a restoration of the complete scale dynamics of the spectrophotometer used, a continuous monitoring of several measuring cells to be used in conjunction with a single apparatus and the possibility of instantaneously bringing about the replacement of a defective light source.

Thus, the invention relates to equipment for in-line spectrophotometric control to be used in conjunction with a double beam spectrophotometer. The double beam spectrophotometer consists of one channel for the reference and one channel for the measurement, an internal emitting light source, a monochromator, a compartment having optical probes and a light detector. The invention has at least one complementary light source emitting through a system of optical fibres permanently towards a reference cell and sequentially towards one of the n measuring cells corresponding to the controls to be performed. The light information from the reference cell and sequentially from each of the n measuring cells being passed by the system of optical fibres respectively to the reference channel and to the measuring channel of the spectrophotometer.

As has been seen, the addition to the commercially used spectrophotometer of an external complementary light source functioning in place of the aforementioned source, makes it possible to adjust the light energy to the particular needs and to make the spectrophotometer operate in a remote manner under light attenuation conditions equivalent to those provided when the analysis was carried out within the sample compartment of the apparatus. Moreover, devices for the sequential switching of the light to each of the measuring cells and then to the measuring channel of the spectrophotometer, make it possible to monitor at n points of an industrial process with the aid of a single spectrophotometer.

According to a preferred embodiment of the invention, the connection between the source and the system of optical fibres is brought about with the aid of a drum or barrel-type rotary system, in which an electric light bulb emits in a first direction towards a fixed exit constituting the reference channel and in the opposite direction across a group of two mirrors at 45° rotated by a stepping motor sequentially towards one of the n exits supplying each of the n measuring cells.

This drum-type switching system displaced by a stepping motor is particularly simple and permits the preceding sequential scanning with perfect reliability and regularity. Moreover, due to the fact that it has a fixed exit for the reference channel makes it possible to permanently illuminate the reference channel without anything between it and the spectrophotometer except for the corresponding optical reference probe.

According to an interesting feature of the invention, the sequential addressing of the light information from the n measuring cells to the single measuring channel of the spectrophotometer is carried out with the aid of a second drum or barrel-type rotary system, which does not have a light source and which is coupled in rotation with the first system, the light travelling in opposite directions in each of the two systems.

The second drum-type system without the light source is consequently used for addressing the $n^{th}$ measuring beam to the measuring channel of the spectrophotometer and as it is mechanically coupled to the stepping motor ensuring the rotation of the first drum-type system, it is ensured that each optical channel is continuous between the light source and measuring channel of the spectrophotometer, successively across each of the n measuring cells.

Finally, according to an important improvement of the present invention, it comprises two identical drum or barrel-type rotary systems provided with a light emitting source, whereof each can be substituted for the other in the case of a failure of one of their light sources, via n+1 three-channel beam switching means, each controlling the addressing of the light circulating on one of the n+1 channels formed by the reference channel and the n measuring channels.

The two identical drum-type systems, each of which has a light source, can be substituted for one another in the case of a failure of the source in use, so that it is ensured that there is no interruption in the measurements and the defective light source can be changed without difficulty following the switching of the device from one rotary system to the other.

DETAILED DESCRIPTION OF THE PREFERRED EMBODIMENTS

Figure 1:
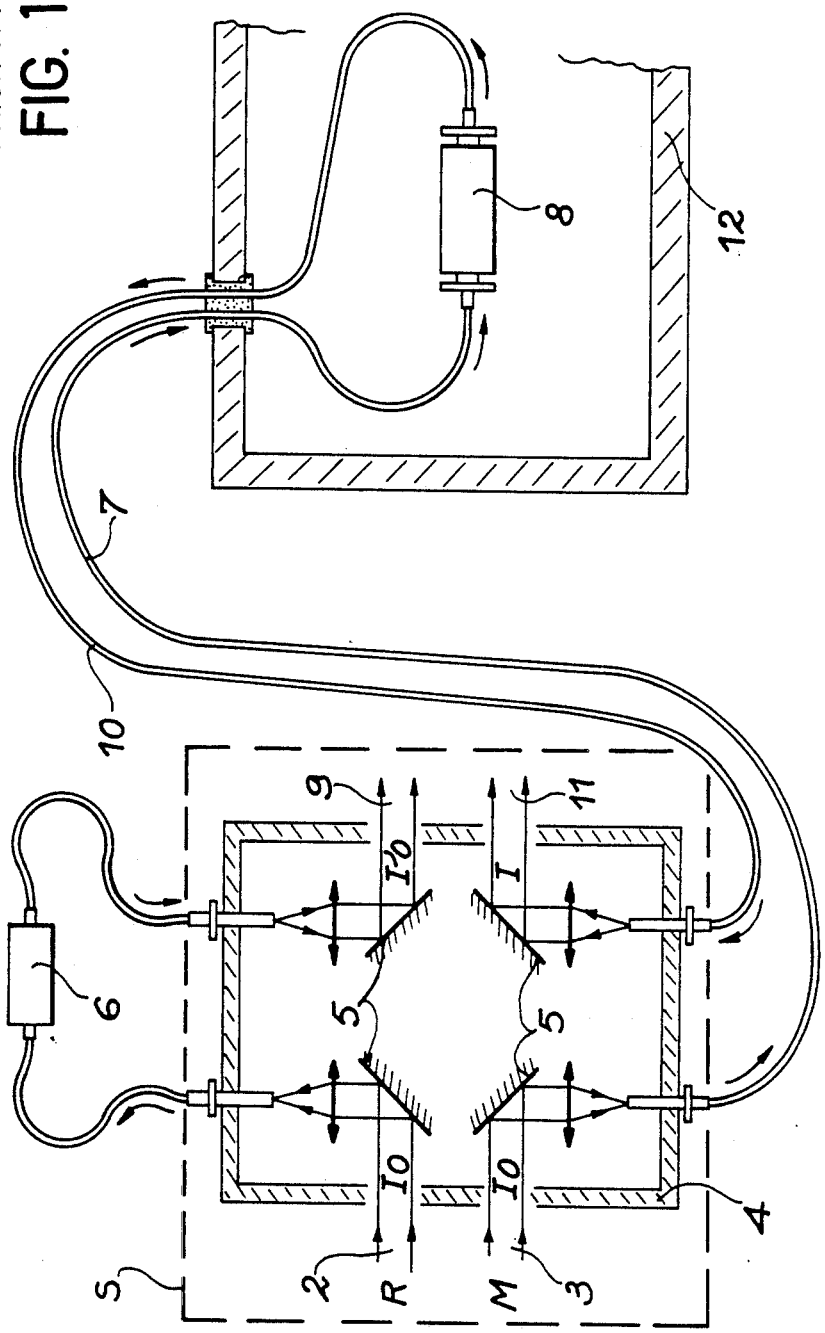
FIG. 1 is a cross-sectional view of a prior art monitoring system
Figure 2:
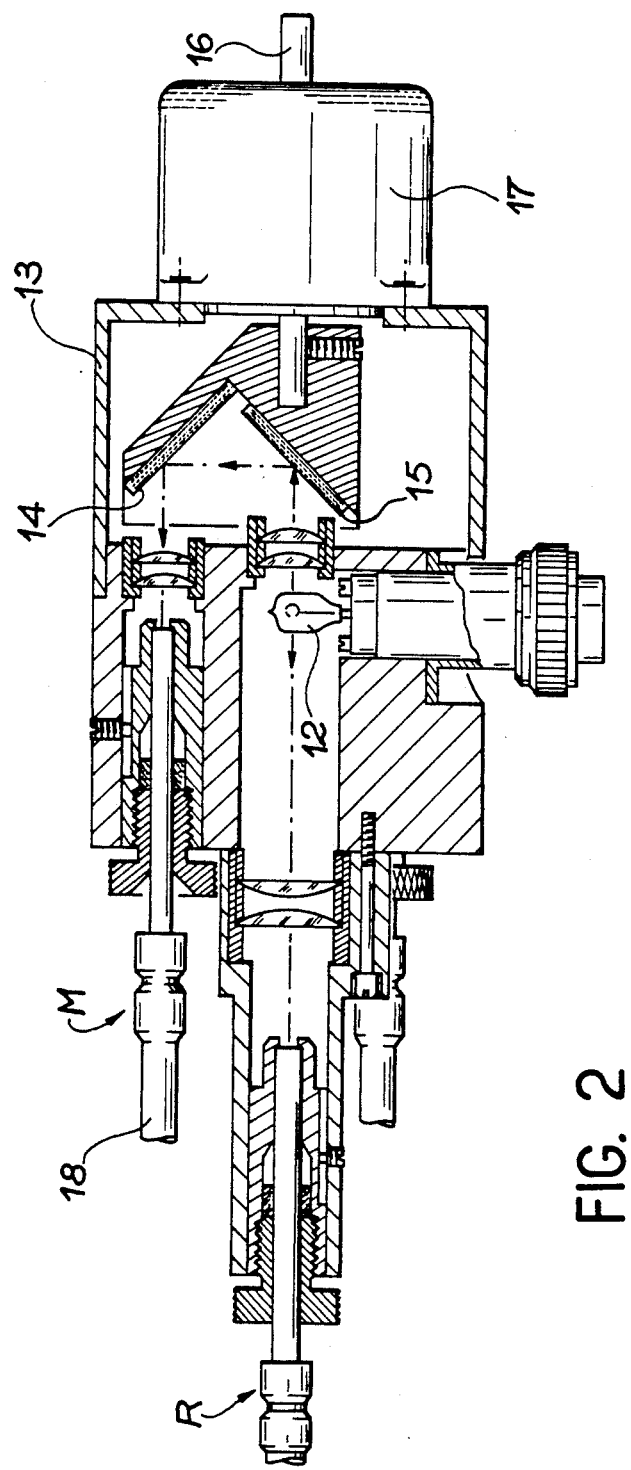
FIG. 2 is a longitudinal sectional view along the axis of the drum-type rotary system equipped with its light bulb.

FIG. 2 shows the light source 12 located in a case 13 and illuminating in opposite directions. The light passes through the fixed reference channel R and simultaneously through a system of mirrors at 45°, 14 and 15, mounted so as to rotate around shaft 16 of stepping motor 17, which directs the light through one of the n measuring channels M arranged circumferentially around the system axis. In FIG. 2 it is only possible to see channel 18, but it is naturally to be assumed that the device has n light exit channels distributed circumferentially around the circumference of the device in the manner of a drum. Thus, the device shown in FIG. 2 constitutes the external auxiliary light source making it possible to reinforce the light flux in the optical fibres and supply to the measuring cell of the spectrophotometer an incident light level identical to that provided for the conditions of use in situ, i.e. without any connection of the spectrophotometer to a system of optical fibres for remotely intercepting information. The light source represented by bulb 12 can emit in the ultraviolet, the visible or the infrared and can be of the quartz-iodine type for visible or near infrared radiation, or of the deuterium type for ultraviolet radiation, but obviously these examples are in no way limitative.

Figure 3:
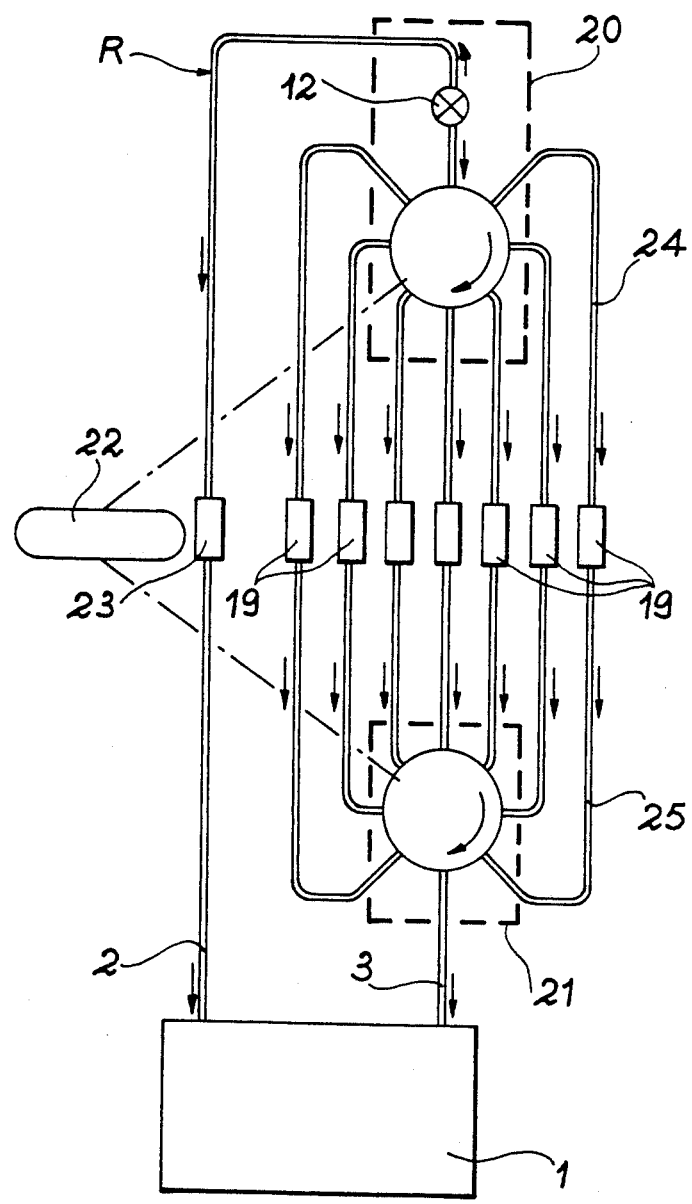
FIG. 3 is a diagrammatic view of seven measuring stations with a reference cell, the assembly being illuminated with the aid of two rotary drum-type systems mechanically mounted on the same shaft and which are consequently integral in rotation.

The device of FIG. 3 illustrates the possibility when using a commercially available spectrophotometer 1 of monitoring seven measuring cells 19 in a sequential manner with the aid of two rotary drum-type systems in accordance with FIG. 2, whereof the first 20 has a light source 12 and whereof the second 21 does not have a light source. The two rotary systems 20, 21 are fitted back to back on the same rotation axis and are consequently mechanically coupled in rotation by a device 22. Reference channel R permanently illuminates the reference cell 23 for checking the turbidity and rotary system 20 successively branches the light to one of the seven optical fibres 24, each leading to one of the seven measuring cells 19. On leaving the measuring cells 19, the optical fibres 24 direct the light to the second rotary system 21 and then on leaving the latter on to the measuring channel 3 of spectrophotometer 1. As can be seen in FIG. 3, the two systems 20, 21, which are coupled in rotation sequentially ensure the light continuity of one of the seven measuring channels between emitting source 20 and the measuring channel 3 of spectrophotometer 1. Each of the two systems 20, 21 is traversed by the light in opposite directions, because the entrances of one precisely correspond to the exits of the other.

Thus, the assembly according to FIG. 3 perfectly effects the continuous measurement of several stations in a remote in-line process with the aid of a single spectrophotometer only having two channels, one for the reference and the other for the measurement. Moreover, the presence of the auxiliary source 12 outside spectrophotometer 1 ensures the total restoration of the scale dynamics of commercial spectrophotometer 1.

Figure 4:
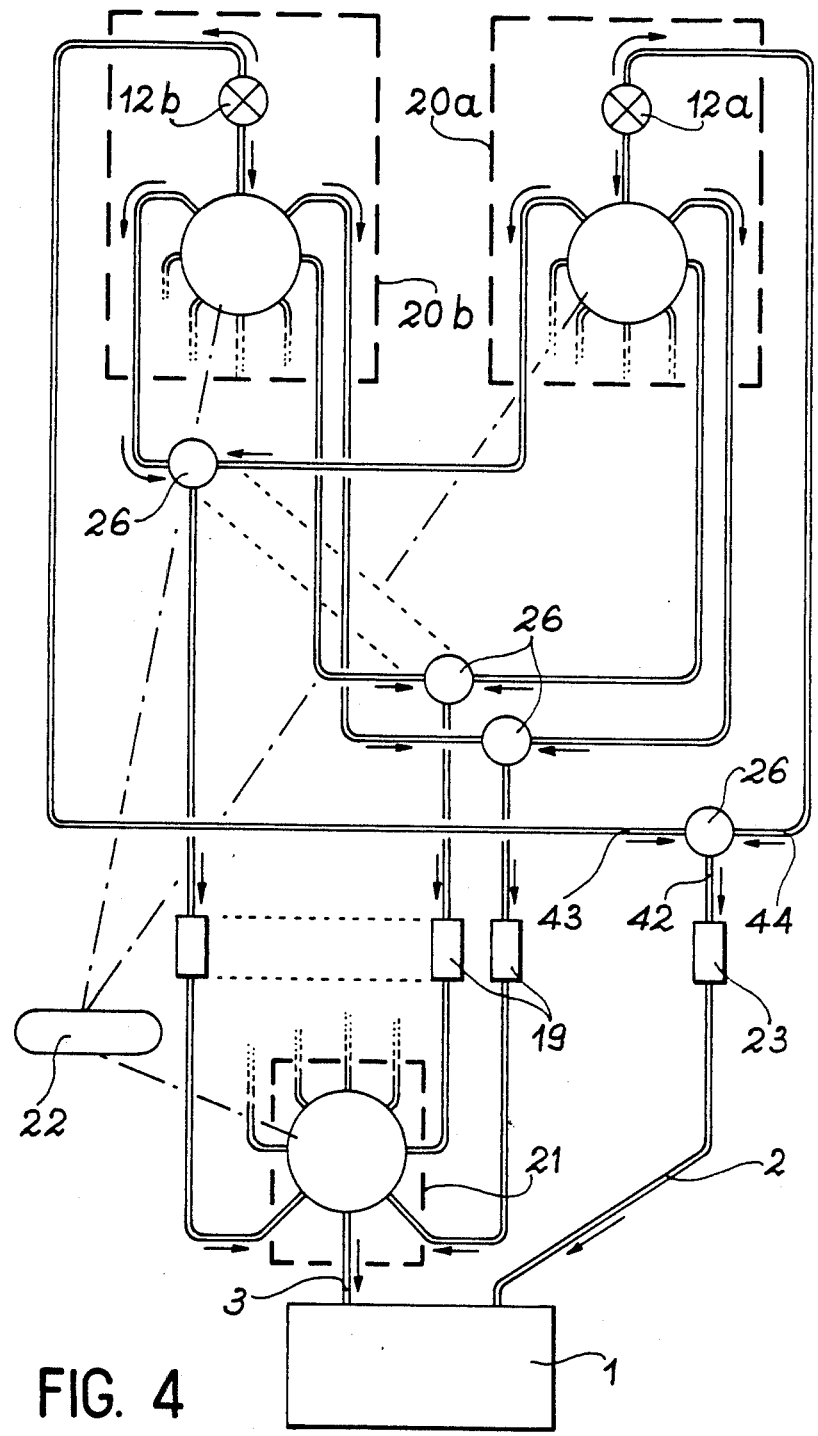
FIG. 4 is diagrammatic view of a second embodiment in which two identical drum-type rotary systems, each having its light source are connected in parallel.

In the assembly of FIG. 4, the same problem is solved and the common elements carry the same reference numerals. However, this assembly differs from the previous assembly in that it has two rotary drum-type systems 20a, 20b, each having its light source 12a, 12b. At all times one of the two systems 20a or 20b functions alone, as a result of the use of switching means for the beams having three channels, such as 26. These switching means 26 supply the light of one of the two systems 20a or 20b to the n measuring cells 19 and the reference cell 23. A third drum-type system 21, which is not provided with a light source, but which is mechanically coupled by the device 22 to one of the two systems 20a, 20b, sequentially the light from one of the seven measuring cells 19 and directs it to the measuring channel 3 of spectrophotometer 1.

Mechanical means according to the prior art and diagrammatically indicated at 22 make it possible to operate one or the other of the sources 20a, 20b in synchronism with system 21.

The operation of the device of FIG. 4 is obvious and it is apparent that, as soon as one of the light sources 12a or 12b is defective, it is merely necessary to act on the switching means of beams 26 for switching the device to the operating systems 20a or 20b. This monitoring and switching can be carried out automatically by a photoelectric cell which monitors the state of each source. Thus, when one of the sources 12a or 12b has proved to be defective, it is merely necessary to replace it in a reasonable time following the incident.

A brief description will now be given with reference to FIGS. 5 and 6 of the possible construction of the three-channel beam switching means 26. Essentially they comprise a reflecting concave mirror 30 mounted within a cylindrical case 31 on a member 32 mounted in bistable manner about axis XX. The switching of the pivoting member 32 is ensured by two springs 33, 34 and the switching travel is limited by regulatable stop screws 35, 36. The switching of the pivoting member is ensured by the tension of springs 33, 34 acting on rod 36 connected to member 32 and the initiation of switching is controlled by two pushing fingers 38, 39, displaced by two plungers 40, 41 which can either be simple hand plungers, or jacks, or electromagnets, or any similar means.

In addition, case 31 is connected to three light access channels, namely a light outlet channel 42 and two light admission channels 43, 44.

Figure 5:
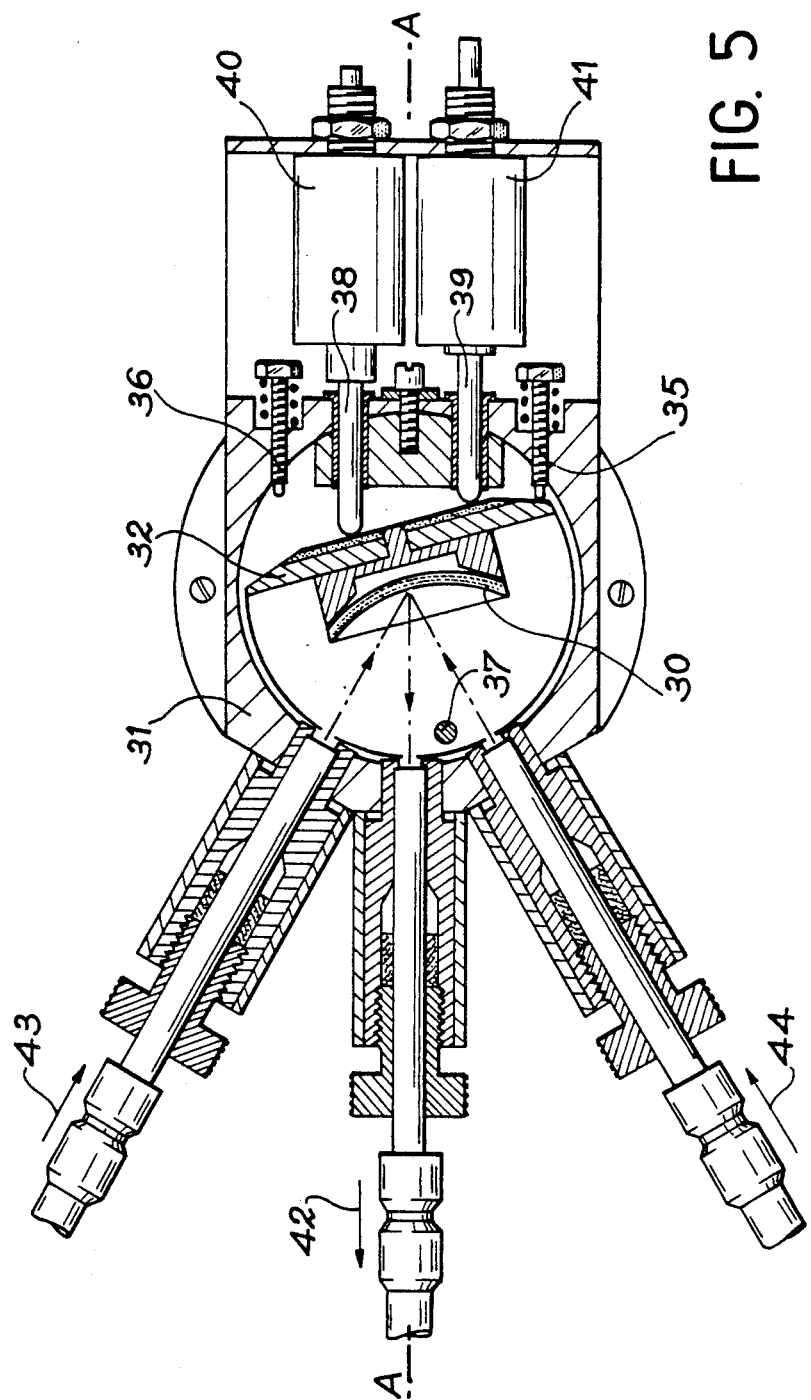
FIG. 5 is a transverse sectional view of one construction of of the switching means of the beam of FIG. 4 shown in section in the plane of the optical junctions.
Figure 6:
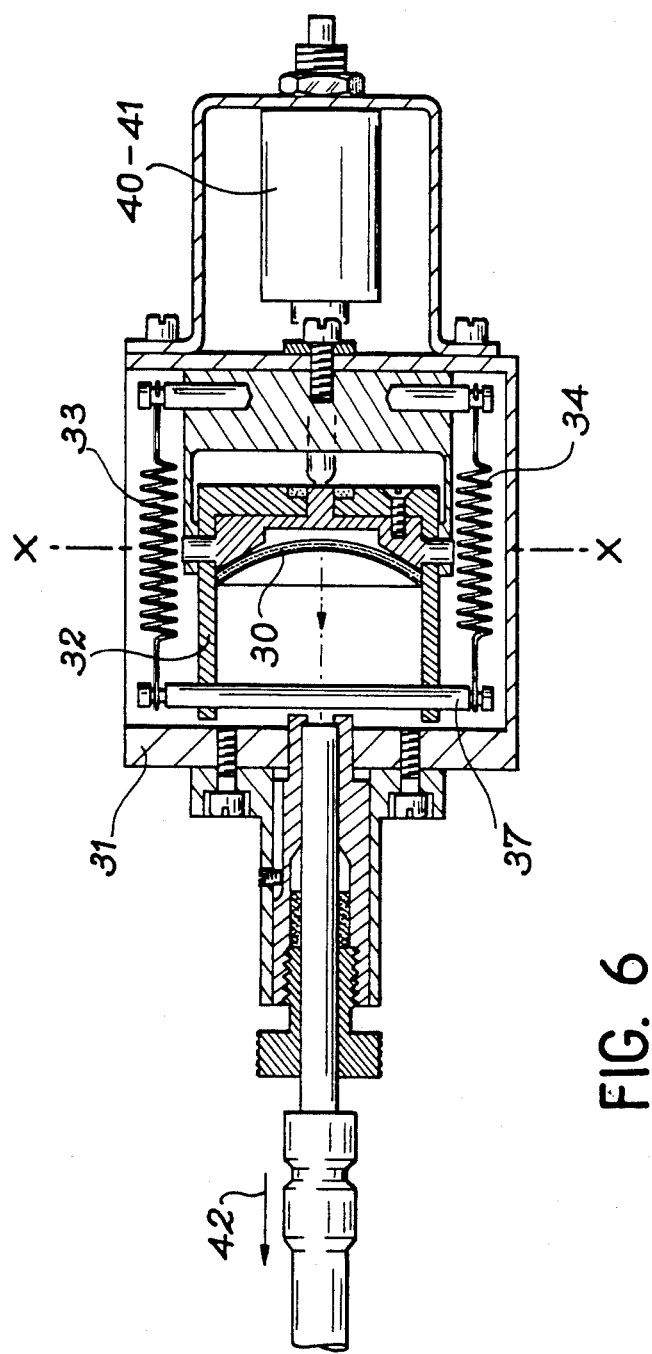
FIG. 6 is a sectional view on line AA of FIG. 5.

The operation of the device according to FIGS. 5 and 6 is easy to understand and can be summarized as follows. The light from the central channel 42 can, as a function of the position of the bistable pivoting member 32 and consequently mirror 30, come either from the admission channel 43, or the admission channel 44. Thus, as required, a three-directional switching means is provided having a fixed starting direction, corresponding in FIG. 4 to the direction in which it is necessary to create a continuous light beam from either channel 43 or 44 to one of the n measuring cells 19. The fixed starting position will depend on which light source 12a or 12b is initially used. For information purposes, references 42, 43 and 44 have been placed on only one of the beam switching means 26 in FIG. 4, but they are obviously all fitted in the same way.

In an application variant of FIG. 4, it can be useful not to have two absolutely identical sources 12a, 12b, but instead one emitting in the ultraviolet and the other emitting in the visible close to the infrared. The system described with reference to FIG. 4 makes it possible to realise such an equipment without modification.

The equipment for the emission and distribution of light by optical fibres according to the invention is applicable to all commercial spectrophotometers, particularly those with a double beam provided that it has an emitting light source, a light monochromator with prisms, networks or filters, a compartment with optical probes, a light detector and its associated electronics.

The measurements performed with the aid of an equipment according to the invention are based on Beer's Law and make it possible to measure the concentration of a product, because this concentration is a function of the logarithm of the ratio of the light intensities Io and I measured before and after passing through each of the optical probes of the different measuring cells.

The optical equipment described hereinbefore with reference to a spectrophotometric installation should not be considered as limited to said application. It also has other interesting applications in all types of remote measurements by optical fibres and particularly e.g. in the measurements of pressures, temperatures or pH-values, if it is wished to sequentially monitor several stations with the aid of a single detector.

What is claimed is:

1. A device for the emission and distribution of light by optical fibres, particularly for in-line spectrophotometric control, to be used in conjunction with a double beam spectrophotometer having one channel for the reference and one channel for the measurement, an internal emitting light source, a monochromator, a compartment having optical probes and a light detector, said device comprising:
   at least one complementary light source emitting through a series of optical fibres;
   means for passing light through one of said series of optical fibres permanently towards a reference cell;
   means for passing light through at least one of the remaining series of optical fibres sequentially towards each of n measuring cells; and
   means including said series of optical fibres for passing light information from the reference cell and sequentially from each of the n measuring cells, respectively, to the reference channel and the measuring channel of the spectrophotometer.

2. A device according to claim 1, wherein said optical fibre means for passing light includes:
   a drum or barrel-type rotary system having n fixed exits in which said complementary light source includes an electric light bulb emitting in one direction towards a fixed exit constituting the reference channel which supplies the reference cell by means of one of said series of optical fibres, and in the opposite direction across a set of two mirrors fixed at 90° to one another, said mirrors being rotated by a stepping motor, and situated so the light strikes said first mirror at a 45° angle thereby directing the light onto the second mirror and sequentially towards each of said n fixed exits constituting the measuring channels which supply each of said n measuring cells by means of the remaining optical fibres of said series of optical fibres with one optical fibre passing from each measuring channel to each of said n measuring cells, respectively.

3. A device according to claim 2, wherein said means for passing light information from each of the n measuring cells includes;
   a second drum or rotary system, which does not have a light source and which has a set of mirrors coupled in rotation with said set of mirrors in said first drum or barrel-type rotary systems, the light traveling in opposite directions in each of the two systems;
   n light access channels used to receive said light information from each of said n measuring cells respectively by means of said series of optical fibres; and
   and at least one additional light access channel used to pass the received light information to the measuring channel of the spectrophotometer.

4. A device according to claim 2, and further comprising:
   a second substantially identical drum or barrel-type rotary system provided with a light source;
   a series of n+1 switching means connected to said series of optical fibres, and
   means for substituting one light source for the other upon the failure of either via said series of n+1 switching means.

* * * * *

UNITED STATES PATENT AND TRADEMARK OFFICE
CERTIFICATE OF CORRECTION

PATENT NO.   : 4,820,045

DATED        : April 11, 1989

INVENTOR(S)  : Boisde et al.

It is certified that error appears in the above-identified patent and that said Letters Patent is hereby corrected as shown below:

Column 5, line 36, delete "24" and insert --25--.

Column 5, line 68, after "sequentially" insert --collects--.

Column 6, line 11, delete "systems" and insert --system--.

Column 8, line 20, delete "systems" and insert --system--.

Signed and Sealed this

Thirty-first Day of October, 1989

Attest:

DONALD J. QUIGG

*Attesting Officer*     *Commissioner of Patents and Trademarks*